(12) United States Patent
Perruna et al.

(10) Patent No.: US 8,933,134 B2
(45) Date of Patent: Jan. 13, 2015

(54) COMPOSITIONS CONTAINING AGAR AND A SOFTENING AGENT

(75) Inventors: Gisela Perruna, Rahway, NJ (US); Dhaval Patel, Edison, NJ (US); Hy Si Bui, Piscataway, NJ (US)

(73) Assignee: L'Oreal, Paris (FR)

( * ) Notice: Subject to any disclaimer, the term of this patent is extended or adjusted under 35 U.S.C. 154(b) by 419 days.

(21) Appl. No.: 13/154,665

(22) Filed: Jun. 7, 2011

(65) Prior Publication Data

US 2011/0306679 A1 Dec. 15, 2011

Related U.S. Application Data

(60) Provisional application No. 61/352,890, filed on Jun. 9, 2010, provisional application No. 61/352,889, filed on Jun. 9, 2010, provisional application No. 61/352,886, filed on Jun. 9, 2010, provisional application No. 61/352,879, filed on Jun. 9, 2010.

(51) Int. Cl.
| | | |
|---|---|---|
| *A61K 8/92* | (2006.01) | |
| *A61K 8/73* | (2006.01) | |
| *A61K 8/41* | (2006.01) | |
| *A61K 8/46* | (2006.01) | |
| *A61K 8/60* | (2006.01) | |
| *A61K 8/898* | (2006.01) | |
| *A61Q 19/00* | (2006.01) | |

(52) U.S. Cl.
CPC . *A61K 8/73* (2013.01); *A61K 8/416* (2013.01); *A61K 8/463* (2013.01); *A61K 8/604* (2013.01); *A61K 8/898* (2013.01); *A61Q 19/00* (2013.01)
USPC .......................................................... 514/777

(58) Field of Classification Search
None
See application file for complete search history.

(56) References Cited

U.S. PATENT DOCUMENTS

| | | | |
|---|---|---|---|
| 4,137,180 A | 1/1979 | Naik et al. | |
| 4,874,554 A | 10/1989 | Lange et al. | |
| 5,356,952 A | 10/1994 | Schmidt | |
| 5,457,083 A | 10/1995 | Muia et al. | |
| 5,540,921 A | 7/1996 | Tanaka | |
| 5,567,808 A | 10/1996 | Desai et al. | |
| 5,618,522 A | 4/1997 | Kaleta et al. | |
| 5,620,682 A | 4/1997 | Fogel | |
| 5,639,733 A | 6/1997 | Koike et al. | |
| 5,645,903 A | 7/1997 | Tanaka et al. | |
| 5,661,149 A | 8/1997 | King et al. | |
| 5,665,292 A * | 9/1997 | Tanaka et al. | 264/86 |
| 5,726,138 A * | 3/1998 | Tsaur et al. | 510/158 |
| 5,756,078 A | 5/1998 | Oppenländer et al. | |
| 5,874,069 A | 2/1999 | Mendolia et al. | |
| 5,876,702 A | 3/1999 | Gers-Barlag et al. | |
| 5,916,577 A | 6/1999 | Golz et al. | |
| 5,919,400 A | 7/1999 | Kim et al. | |
| 5,919,441 A | 7/1999 | Mendolia et al. | |
| 5,928,655 A | 7/1999 | Avalle | |
| 5,961,990 A | 10/1999 | Delrieu et al. | |
| 5,981,680 A | 11/1999 | Petroff et al. | |
| 6,051,216 A | 4/2000 | Barr et al. | |
| 6,114,366 A | 9/2000 | Lutz et al. | |
| 6,121,302 A | 9/2000 | Rothenburger et al. | |
| 6,123,953 A | 9/2000 | Greff | |
| 6,309,628 B1 | 10/2001 | Ansmann et al. | |
| 6,319,507 B1 | 11/2001 | Delrieu et al. | |
| 6,338,839 B1 | 1/2002 | Auguste et al. | |
| 6,391,319 B1 | 5/2002 | Kröpke et al. | |
| 6,599,513 B2 | 7/2003 | Deckers et al. | |
| 6,673,863 B2 | 1/2004 | Travkina et al. | |
| 6,723,311 B1 | 4/2004 | Seipel et al. | |
| 6,800,293 B1 | 10/2004 | Farby et al. | |
| 6,830,746 B2 | 12/2004 | SaNogueira et al. | |
| 6,878,378 B1 | 4/2005 | Yamaki et al. | |
| 6,881,399 B2 | 4/2005 | Milbradt et al. | |
| 6,905,694 B1 | 6/2005 | Modi | |
| 7,108,860 B2 | 9/2006 | Dueva et al. | |
| 7,175,834 B2 | 2/2007 | Aust et al. | |
| 7,192,599 B2 | 3/2007 | Mercier et al. | |
| 7,235,251 B2 | 6/2007 | Hamer et al. | |
| 7,297,668 B2 | 11/2007 | Johansson et al. | |
| 7,309,496 B2 | 12/2007 | Johansson et al. | |
| 7,374,771 B2 | 5/2008 | Eversheim et al. | |
| 7,384,646 B2 | 6/2008 | Kobayashi et al. | |
| 7,399,479 B2 | 7/2008 | Maillefer et al. | |
| 7,416,719 B2 | 8/2008 | Huerta et al. | |
| 7,488,471 B2 | 2/2009 | Mercier et al. | |
| 2001/0021711 A1 | 9/2001 | Beilfuss et al. | |

(Continued)

FOREIGN PATENT DOCUMENTS

| | | |
|---|---|---|
| CN | 1650845 | 8/2005 |
| CN | 1942170 | 4/2007 |
| DE | 4140474 | 6/1993 |
| DE | 19548345 | 6/1997 |
| DE | 20009445 | 8/2000 |
| DE | 10033975 | 1/2002 |
| DE | 10044062 | 4/2002 |
| DE | 10150728 | 4/2003 |
| DE | 10224979 | 12/2003 |
| DE | 10252757 | 6/2004 |

(Continued)

OTHER PUBLICATIONS

Google translate, agar, 2013.*

(Continued)

*Primary Examiner* — Susan Tran
*Assistant Examiner* — William Craigo
(74) *Attorney, Agent, or Firm* — Oblon, Spivak, McClelland, Maier & Neustadt, L.L.P.

(57) ABSTRACT

The present invention includes a composition that has (a) at least one thermo-reversible polysaccharide chosen from agar; (b) at least one softening agent chosen from a cationic surfactant, an anionic surfactant, a nonionic esterified sugar surfactant, a polyorganosiloxane-containing polymer, a sugar silicone surfactant, and mixtures thereof; (c) at least one oil; and (d) water.

15 Claims, No Drawings

(56) References Cited

U.S. PATENT DOCUMENTS

| | | |
|---|---|---|
| 2002/0159960 A1 | 10/2002 | Scancarella et al. |
| 2004/0018219 A1 | 1/2004 | Mateu et al. |
| 2004/0028637 A1 | 2/2004 | Villard et al. |
| 2004/0052827 A1 | 3/2004 | Winkler et al. |
| 2004/0059006 A1 | 3/2004 | Beilfuss et al. |
| 2004/0063806 A1 | 4/2004 | Kaarnakari |
| 2004/0152748 A1 | 8/2004 | Diehl et al. |
| 2004/0197294 A1 | 10/2004 | Seipel et al. |
| 2004/0228820 A1 | 11/2004 | Elliott et al. |
| 2005/0048139 A1 | 3/2005 | Modak et al. |
| 2005/0100569 A1 | 5/2005 | Mercier et al. |
| 2005/0106191 A1 | 5/2005 | Kobayashi et al. |
| 2005/0196347 A1 | 9/2005 | Berillouet et al. |
| 2005/0222276 A1 | 10/2005 | Schmaus et al. |
| 2005/0226832 A1 | 10/2005 | Bobka et al. |
| 2005/0228032 A1 | 10/2005 | Merianos et al. |
| 2005/0238677 A1 | 10/2005 | Mercier et al. |
| 2005/0271612 A1 | 12/2005 | Bobka et al. |
| 2006/0003948 A1 | 1/2006 | Krasutsky et al. |
| 2006/0045893 A1 | 3/2006 | Yu et al. |
| 2006/0051383 A1 | 3/2006 | Emig et al. |
| 2006/0110345 A1* | 5/2006 | Lu et al. ............ 424/64 |
| 2006/0127272 A1 | 6/2006 | Saitmacher et al. |
| 2006/0153792 A1 | 7/2006 | Arnaud et al. |
| 2006/0177471 A1 | 8/2006 | Wagh |
| 2006/0189662 A1 | 8/2006 | Goto et al. |
| 2006/0275234 A1 | 12/2006 | Dierker et al. |
| 2007/0009450 A1 | 1/2007 | Emig |
| 2007/0081953 A1 | 4/2007 | Dahms |
| 2007/0092462 A1 | 4/2007 | Gans Russ et al. |
| 2007/0092470 A1 | 4/2007 | Allef et al. |
| 2007/0092478 A1 | 4/2007 | Behrens et al. |
| 2007/0104665 A1 | 5/2007 | Jones et al. |
| 2007/0116662 A1 | 5/2007 | Zielinski et al. |
| 2007/0140984 A1 | 6/2007 | Kusano et al. |
| 2007/0178144 A1 | 8/2007 | Hameyer et al. |
| 2007/0190005 A1 | 8/2007 | Rozsa et al. |
| 2007/0207105 A1 | 9/2007 | Winn |
| 2007/0265352 A1 | 11/2007 | Roeding et al. |
| 2007/0286826 A1 | 12/2007 | Grune |
| 2007/0298000 A1 | 12/2007 | Grune |
| 2007/0298002 A1 | 12/2007 | Barone |
| 2008/0051492 A1 | 2/2008 | Mitarotonda et al. |
| 2008/0095719 A1 | 4/2008 | Herrmann et al. |
| 2008/0108709 A1 | 5/2008 | Meyer et al. |
| 2008/0139672 A1 | 6/2008 | Rozsa et al. |
| 2008/0196174 A1 | 8/2008 | Schmenger et al. |
| 2008/0199417 A1* | 8/2008 | Joffre et al. ............ 424/70.12 |
| 2008/0233060 A1 | 9/2008 | Grune |
| 2008/0249136 A1 | 10/2008 | Annis et al. |
| 2008/0254150 A1 | 10/2008 | Rheins et al. |
| 2008/0255247 A1 | 10/2008 | Sagalowicz et al. |
| 2008/0275113 A1 | 11/2008 | Huetter et al. |
| 2009/0169501 A1* | 7/2009 | Feng et al. ............ 424/70.7 |

FOREIGN PATENT DOCUMENTS

| | | |
|---|---|---|
| DE | 102005011626 | 9/2006 |
| DE | 102005051862 | 4/2007 |
| EP | 0519727 | 12/1992 |
| EP | 0547897 | 6/1993 |
| EP | 0615744 | 9/1994 |
| EP | 0553241 | 4/1995 |
| EP | 0770382 | 5/1997 |
| EP | 0773017 | 5/1997 |
| EP | 773018 | 5/1997 |
| EP | 0776657 | 6/1997 |
| EP | 0803245 | 10/1997 |
| EP | 814762 | 1/1998 |
| EP | 0890328 | 1/1999 |
| EP | 1051965 | 11/2000 |
| EP | 1157687 | 11/2001 |
| EP | 1238651 | 9/2002 |
| EP | 979066 | 1/2004 |
| EP | 1426029 | 6/2004 |
| EP | 1465486 | 10/2004 |
| EP | 1235553 | 11/2004 |
| EP | 1477157 | 11/2004 |
| EP | 1537854 | 6/2005 |
| EP | 1593371 | 11/2005 |
| EP | 1313443 | 12/2005 |
| EP | 1652435 | 5/2006 |
| EP | 1661552 | 5/2006 |
| EP | 1731134 | 12/2006 |
| EP | 1734922 | 12/2006 |
| EP | 1743628 | 1/2007 |
| EP | 1779835 | 5/2007 |
| EP | 1813311 | 8/2007 |
| EP | 1870078 | 12/2007 |
| EP | 1889596 | 2/2008 |
| EP | 1920756 | 5/2008 |
| EP | 1461004 | 12/2008 |
| ES | 2256283 | 7/2006 |
| FR | 2846234 | 4/2004 |
| FR | 2876004 | 4/2006 |
| FR | 2883741 | 10/2006 |
| FR | 2888504 | 1/2007 |
| GB | 2437149 | 10/2007 |
| JP | 61263906 | 11/1986 |
| JP | 1038082 | 2/1989 |
| JP | 2083309 | 3/1990 |
| JP | 3161417 | 7/1991 |
| JP | 5279651 | 10/1993 |
| JP | 6068608 | 3/1994 |
| JP | 7017828 | 1/1995 |
| JP | 9124435 | 5/1997 |
| JP | 9157149 | 6/1997 |
| JP | 10114624 | 5/1998 |
| JP | 10279917 | 10/1998 |
| JP | 11092333 | 4/1999 |
| JP | 11106313 | 4/1999 |
| JP | 11322591 | 11/1999 |
| JP | 2001131528 | 5/2001 |
| JP | 2001199828 | 7/2001 |
| JP | 2001233741 | 8/2001 |
| JP | 2001302492 | 10/2001 |
| JP | 2002003330 | 1/2002 |
| JP | 2002080320 | 3/2002 |
| JP | 2002322026 | 11/2002 |
| JP | 2003095862 | 4/2003 |
| JP | 2003300856 | 10/2003 |
| JP | 2004043336 | 2/2004 |
| JP | 2004099588 | 4/2004 |
| JP | 2005023083 | 1/2005 |
| JP | 2005097148 | 4/2005 |
| JP | 2005509617 | 4/2005 |
| JP | 2005511757 | 4/2005 |
| JP | 2005213174 | 8/2005 |
| JP | 2005306849 | 11/2005 |
| JP | 2007022950 | 2/2007 |
| JP | 2007084464 | 4/2007 |
| JP | 2007145748 | 6/2007 |
| JP | 2007161654 | 6/2007 |
| JP | 2007169184 | 7/2007 |
| JP | 2007186465 | 7/2007 |
| JP | 2007197322 A * | 9/2007 |
| JP | 2007269760 | 10/2007 |
| JP | 2007269813 | 10/2007 |
| JP | 2007277141 | 10/2007 |
| JP | 2007277142 | 10/2007 |
| JP | 4035258 | 1/2008 |
| JP | 4091559 (B2) | 5/2008 |
| JP | 4122272 (B2) | 7/2008 |
| WO | WO96/29048 | 9/1996 |
| WO | WO98/50000 | 11/1998 |
| WO | WO0113864 | 3/2001 |
| WO | WO03/042221 | 5/2003 |
| WO | WO2004050045 | 6/2004 |

(56) References Cited

FOREIGN PATENT DOCUMENTS

| | | |
|---|---|---|
| WO | WO2005070384 | 8/2005 |
| WO | WO2005087182 | 9/2005 |
| WO | WO2005102276 | 11/2005 |
| WO | WO2007044487 | 4/2007 |
| WO | WO2007051586 | 5/2007 |
| WO | WO2007071089 | 6/2007 |
| WO | WO 2008013106 A1 * | 1/2008 |
| WO | WO2008018644 | 2/2008 |
| WO | WO2008071027 | 6/2008 |
| WO | WO2008095796 | 8/2008 |

OTHER PUBLICATIONS

Google translate, vegetable gelatin, 2013.*
Google Translate, Tobe, JP2007197332A, Paragraph 0021, 2013.*
JP-2007-197332-A.*
The Cooks Thesaurus, 2012.*
U.S. Appl. No. 13/154,793, filed Jun. 7, 2011, Perruna, et al.

* cited by examiner

COMPOSITIONS CONTAINING AGAR AND A SOFTENING AGENT

CROSS-REFERENCE TO RELATED APPLICATIONS

This application claims the benefit of priority under 35 U.S.C. §119(e) from U.S. Provisional Application Ser. Nos. 61/352,890; 61/352,889; 61/352,886; and 61/352,879, all filed Jun. 9, 2010, the entire contents of which are hereby incorporated by reference.

FIELD OF THE INVENTION

The current invention is directed toward compositions, preferably personal care compositions, containing a material which is organic, sustainable and thermo-reversible.

BACKGROUND

Agar is a known thermo-reversible polysaccharide derived from red algae, also known as seaweed. It is utilized in the pharmaceutical industry and in the food industry as a gellant or thickener when used in association with water.

The use of agar as a gellant is known to produce very rigid/hard gelled compositions. Such rigidity prevents the product from being easily retrieved from its container by either an applicator or a consumer's finger, a phenomenon commonly referred to in the industry as poor "pickup".

The use of agar is also known to oftentimes result in the formation of craters on a resultant product's surface which is undesirable from an aesthetic standpoint. Moreover, the breaking of the product's surface during retrieval from its container oftentimes causes the product to crumble.

Therefore, a need exists to be able to incorporate agar into personal care compositions without the attendant problems of extreme rigidity, poor pickup, crater formation and crumbling.

SUMMARY OF THE INVENTION

The present invention is directed to a composition comprising: (a) at least one thermo-reversible polysaccharide chosen from agar; (b) at least one softening agent chosen from a cationic surfactant, an anionic surfactant, a nonionic esterified sugar surfactant, a polyorganosiloxane-containing polymer, a sugar silicone surfactant, and mixtures thereof; (c) at least one oil; and (d) water. Where the softening agent is a polyorganosiloxane-containing polymer and/or a sugar silicone surfactant, the composition preferably further comprises at least one emulsifier different from (b).

The present invention is also directed to a process for softening an emulsion containing agar by adding to the emulsion: a) at least one softening agent chosen from a cationic surfactant, an anionic surfactant, a nonionic esterified sugar surfactant, a polyorganosiloxane-containing polymer, a sugar silicone surfactant, and mixtures thereof. Where the softening agent is a polyorganosiloxane-containing polymer and/or a sugar silicone surfactant, the composition preferably further comprises at least one emulsifier different from the softening agent.

The present invention is also directed to a process for making a composition comprising mixing together: (a) at least one thermo-reversible polysaccharide chosen from agar; (b) at least one softening agent chosen from a cationic surfactant, an anionic surfactant, a nonionic esterified sugar surfactant, a polyorganosiloxane-containing polymer, a sugar silicone surfactant, and mixtures thereof; (c) at least one oil; and (d) water. Where the softening agent is a polyorganosiloxane-containing polymer and/or a sugar silicone surfactant, the composition preferably further comprises at least one emulsifier different from (b). Such compositions a soft texture, good pickup and a desirable aesthetic appearance.

It has been surprisingly found that by employing certain types of compounds as softening agents in a composition, preferably an emulsion, containing agar, the resultant composition possesses a soft texture, resistance to crumbling and improved pickup.

DETAILED DESCRIPTION

Other than in the operating examples, or where otherwise indicated, all numbers expressing quantities of ingredients and/or reaction conditions are to be understood as being modified in all instances by the term "about," meaning within 10% to 15% of the indicated number.

Generally, the present invention relates to emulsions, preferably oil-in-water emulsions, that use agar as a gelling agent. It has been surprisingly found that the associations of agar with certain types of softening agents, described herein, provide unique advantages. Particularly preferred softening agents include: cationic surfactants; anionic surfactants; nonionic esterified sugar surfactants; polyorganosiloxane-containing polymers; sugar silicone surfactants; and mixtures thereof.

Without intending to be bound by theory, it is believed that when agar is used to gellify water-containing compositions, numerous hydrogen bonds are formed between the agar and the water molecules, resulting in the compositions becoming undesirably rigid, thereby yielding poor pickup, surface cratering and product crumbling. Adding the subject softening agents addresses such problems associated with agar-containing compositions.

Agar

According to the present invention, compositions comprising agar are provided. Chemically, agar is a polymer made up of subunits of the sugar galactose. Agar consists of a mixture of agarose and agaropectin. Agarose is a linear polymer, having a molecular weight of about 120,000. Agaropectin is a heterogeneous mixture of smaller molecules that occur in lesser amounts. Their structures are similar but slightly branched and sulfated, and they may have methyl and pyruvic acid ketal substituents.

Suitable agars include, for example, pharmaceutical grade agars. Pharmaceutical grade agar is defined as having been tested for safety, potency, purity and efficacy.

A preferred agar is AGAR AGAR IRX 23900, commercially available from CNI-Colloides Naturels International. Other preferred agars are Agar RS-100, Agar Agar 100 FCC/NF Powder, Agar Agar 150 FCC/NF Powder, all commercially available from TIC Gums. Still another preferred agar is Agar Agar Thermically Treated, commercially available from Setal G. A preferred pharmaceutical grade agar is Pharmaceutical Agar, commercially available from TIC Gums.

Preferably, the agar is employed in an amount ranging from about 0.1 to about 3% by weight, preferably from about 0.15 to about 2% by weight, and preferably from about 0.2 to about 1.0% by weight, including all ranges and subranges therebetween, all weights based on the total weight of the composition.

Softening Agent

According to the present invention, compositions comprising at least one softening agent are provided. In accordance with the present invention, the at least one softening agent is chosen from a cationic surfactant, an anionic surfactant, a nonionic esterified sugar surfactant, a polyorganosiloxane-containing polymer, a sugar silicone surfactant, and mixtures thereof. In accordance with the present invention, the softening agents are present in an amount effective to soften a composition containing agar.

Cationic Surfactants, Anionic Surfactants and Nonionic Surfactants

According to preferred embodiments, softening agents of the present invention are chosen from cationic surfactants, anionic surfactants, a nonionic esterified sugar surfactants, and mixtures thereof.

Cationic Surfactants

The cationic surfactants can include, for example, a mixture of quaternary ammonium mono-, di- and triester salts with a weight majority of diester salts.

Examples of mixtures of ammonium salts that may be used include the mixture containing 15% to 30% by weight of acyloxyethyl-dihydroxyethyl-methylammonium methyl sulfate, 45% to 60% of diacyloxyethyl-hydroxyethyl-methylammonium methyl sulfate and 15% to 30% of triacyloxyethyl-methylammonium methyl sulfate, the acyl radicals containing from 14 to 18 carbon atoms and being derived from optionally, partially hydrogenated palm oil. It is also possible to use the ammonium salts containing at least one ester function described in U.S. Pat. No. 4,874,554 and U.S. Pat. No. 4,137,180, incorporated in their entirety by reference herein.

Mention may also be made of salts (and especially the methosulfates) of dipalmitoylethylhydroxymethylammonium, salts (and especially the chlorides) of tetraalkylammonium, for instance salts (and especially the chlorides) of dialkyldimethylammonium or alkyltrimethylammonium in which the alkyl radical contains from about 12 to 22 carbon atoms, in particular behenyltrimethylammonium, distearyldimethylammonium, cetyltrimethylammonium or benzyldimethylstearylammonium salts (and especially the chlorides), or alternatively, secondly of salts (and especially the chlorides) of palmitylamidopropyltrimethylammonium or salts (and especially the chlorides) of stearamidopropyldimethyl(myristyl acetate) ammonium, and especially the stearamidopropyldimethyl(myristyl acetate) ammonium chloride sold under the name Ceraphyl® 70 by the company Van Dyk.

The cationic surfactants that are preferred in the composition of the invention are chosen from quaternary ammonium salts, and in particular from behenyltrimethylammonium chloride, dipalmitoylethylhydroxyethylmethylammonium methosulfate, cetyltrimethylammonium chloride, Quaternium-83, behenylamidopropyl-2,3-dihydroxypropyldimethylammonium chloride and palmitylamidopropyltrimethylammonium chloride.

A particularly preferred cationic surfactant is behentrimonium chloride, commercially available under the tradename VARISOFT® BT 85.

Anionic Surfactants

Suitable anionic surfactants include, for example, salts (such as alkaline salts, for example sodium salts, ammonium salts, amine salts, amino alcohol salts, and magnesium salts) of the following compounds: alkyl sulphates, alkyl ether sulphates, alkylamido ether sulphates, alkylaryl polyether sulphates, monoglyceride sulphates, alkyl sulphonates, alkyl phosphates, alkylamide sulphonates, alkylaryl sulphonates, α-olefin sulphonates, paraffin sulphonates, alkyl sulphosuccinates, alkyl ether sulphosuccinates, alkylamide sulphosuccinates, alkyl sulphosuccinamates, alkyl sulphoacetates, alkyl ether phosphates, acyl sarcosinates, acyl isethionates, and N-acyltaurates, wherein the alkyl or acyl radical of all of these various compounds may have from 12 to 20 carbon atoms, and the aryl radical may be chosen from phenyl and benzyl groups. Among the at least one anionic surfactant that may be used, mention may also be made of fatty acid salts such as the salts of oleic, ricinoleic, palmitic, and stearic acids; coconut oil acid; hydrogenated coconut oil acid; and acyl lactylates in which the acyl radical contains 8 to 20 carbon atoms. Use may also be made of at least one weakly anionic surfactant, such as alkyl-D-galactosiduronic acids and their salts, and polyoxyalkylenated carboxylic ether acids and their salts, such as those containing from 2 to 50 ethylene oxide groups. Anionic surfactants of the polyoxyalkylenated carboxylic ether acid or salt type may, for example, correspond to formula (I) below:

$$R_1-(OC_2H_4)_n-OCH_2COOA \quad (1)$$

in which:

$R_1$ is chosen from alkyl, alkylamido, and alkaryl groups, and n is chosen from integers and decimal numbers (average value) that may range from 2 to 24, such as from 3 to 10, wherein the alkyl radical has between 6 and 20 carbon atoms approximately, and the aryl radical may be a phenyl;

A is chosen from hydrogen, ammonium, Na, K, Li, Mg, monoethanolamine, and triethanolamine residues. Mixtures of compounds of formula (I) can also be used, for example mixtures in which the groups $R_1$ are different.

Compounds of formula (I) are sold, for example, by the company Chem Y under the name Akypo® (NP40, NP70, OP40, OP80, RLM25, RLM38, RLMQ 38 NV, RLM 45, RLM 45 NV, RLM 100, RLM 100 NV, RO 20, RO 90, RCS 60, RS 60, RS 100, and RO 50) and by the company Sandoz under the name Sandopan® (DTC Acid and DTC).

A particularly preferred anionic surfactant is sodium laureth sulfate, commercially available under the tradename GENAPOL® LRO L'O.

Nonionic Surfactants

Suitable nonionic surfactants are those chosen from at least esterified sugar surfactants. Examples of suitable esterified sugar surfactants include sucrose stearate, dextrin palmitate, and mixtures thereof.

Particularly preferred esterified sugar surfactants include sucrose stearate, commercially available under the tradename RYOTO® SUGAR ESTER S 1570, and dextrin palmitate, commercially available under the tradename RHEOPEARL® TL2-OR.

Preferably, the softening agent, chosen from a cationic surfactant, an anionic surfactant, a nonionic esterified sugar surfactant, and mixtures thereof, is employed in an amount ranging from about 0.1 to about 6% by weight, preferably from about 0.2 to about 4% by weight, and more preferably from about 1 to about 3% by weight, including all ranges and subranges therebetween, all weights based on the total weight of the composition.

Further, preferably, the esterified sugar surfactant is employed in an amount ranging from about 0.1 to about 5% by weight, preferably from about 0.2 to about 4% by weight, and more preferably from about 0.5 to about 2% by weight, including all ranges and subranges therebetween, all weights based on the total weight of the composition.

Polyorganosiloxane-Containing Polymers

Softening agents of the present invention can also be a polyorganosiloxane-containing polymer.

The polyorganosiloxane-containing polymer useful herein is a polymer (homopolymer or copolymer) having at least one moiety which contains: at least one polyorganosiloxane group consisting of 1 to about 1000 organosiloxane units in the chain of the moiety or in the form of a graft, and at least two groups capable of establishing hydrogen interactions.

The polyorganosiloxane-containing polymers may comprise at least one moiety corresponding to formula (I):

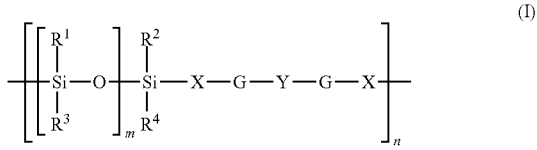

in which:
1) $R^1$, $R^2$, $R^3$ and $R^4$, which may be identical or different, represent a group chosen from:
   (a) linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms,
   (b) $C_6$ to $C_{10}$ aryl groups, optionally substituted with one or more $C_1$ to $C_4$ alkyl groups,
   (c) polyorganosiloxane chains possibly containing one or more oxygen, sulphur and/or nitrogen atoms;
2) X, which may be identical or different, represents a linear or branched $C_1$ to $C_{30}$ alkylenediyl group, possibly containing in its chain one or more oxygen and/or nitrogen atoms;
3) Y is a saturated or unsaturated, $C_1$ to $C_{50}$ linear or branched divalent alkylene, arylene, cycloalkylene, alkylarylene or arylalkylene group, optionally comprising one or more oxygen, sulphur and/or nitrogen atoms, and/or optionally substituted with one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with one to three $C_1$ to $C_3$ alkyl, $C_1$ to $C_3$ hydroxyalkyl, and $C_1$ to $C_6$ aminoalkyl groups;
4) G, which may be identical or different, represents a group chosen from ester, amide, sulphonamide, carbamate, thiocarbamate, urea, thiourea groups, and combinations thereof;
5) m is an integer ranging from 1 to 1,000, preferably from 1 to 700 and more preferably from 6 to 200; and
6) n is an integer ranging from 2 to 500 and preferably from 2 to 200.

The polyorganosiloxane-containing polymers may also comprise at least one moiety corresponding to formula (II):

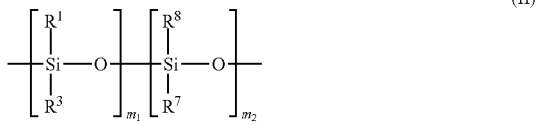

in which
$R^1$ and $R^3$, which may be identical or different, are as defined above for formula (I),
$R^7$ represents a group as defined above for $R^1$ and $R^3$, or represents a group of formula —X-G-$R^9$ in which X and G are as defined above for formula (I) and $R^9$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, $R^8$ represents a group of formula —X-G-$R^9$ in which X, G and $R^9$ are as defined above,
$m_1$ is an integer ranging from 1 to 998, and
$m_2$ is an integer ranging from 2 to 500.

According to another embodiment, it is also possible to use a copolymer comprising several different moieties of formula (I), and/or several different moieties of formula (II), that is to say a polymer in which at least one of the groups R1, R2, R3, R4, X, G, Y, m and n is different in one of the moieties.

It is also possible to use a copolymer comprising at least one moiety of formula (I) and at least one moiety of formula (II), the moieties of formula (I) and the moieties of formula (II) possibly being identical to, or different from, each other. These copolymers may be block copolymers or grafted copolymers.

Additional polyorganosiloxane-containing polymers which may be used in the composition of the invention include those described in documents U.S. Pat. No. 5,874,069, U.S. Pat. No. 5,919,441, U.S. Pat. No. 6,051,216, and U.S. Pat. No. 5,981,680, the entire contents of which are hereby incorporated by reference.

A preferred polyorganosiloxane-containing polymer for use in the present invention will have at least one moiety chosen from formula (III):

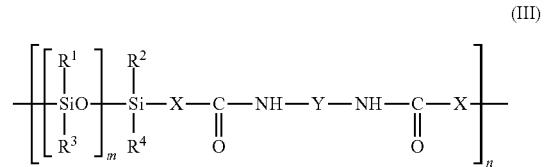

and formula (IV)

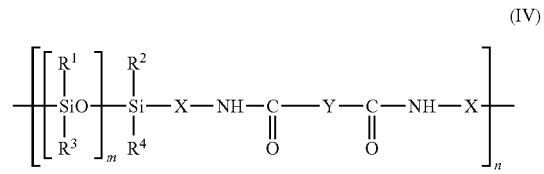

in which:
(a) $R^1$, $R^2$, $R^3$ and $R^4$ are the same or different and may be selected from the group consisting of methyl, ethyl, propyl, isopropyl, a siloxane chain, and phenyl;
(b) X is a linear or branched chain alkylene having 1-30 carbons;
(c) Y is selected from the group consisting of linear or branched chain alkylenes having 1-40 carbons;
(d) m is a number between 1 and 700;
(e) n is a number between 1 and 500.

Particularly preferred polyorganosiloxane-containing polymers useful herein are commercially available from Dow Corning as DC 8178 and DC 8179, which are known under the INCI denomination of Nylon-611/Dimethicone Copolymer.

Preferably, the polyorganosiloxane-containing polymer is employed in an amount ranging from about 0.2 to about 10% by weight, preferably from about 0.5 to about 5% by weight, and more preferably from about 1 to about 2% by weight, including all ranges and subranges therebetween, all weights based on the total weight of the composition.

Sugar Silicone Surfactants

Softening agents of the present invention can also be a sugar silicone surfactant.

The sugar silicone surfactant of the present invention has the following formula:

Sach-X-Dn-X-Sach where Sach represents a saccharide moiety containing multiple hydroxyl groups. Suitable saccharide moieties include, but are not limited to, those based on monosaccharides such as, for example, glucose, fructose, galactose, ribose, mannose, sorbose, etc., and those based one oligosaccharides such as, for example, sucrose, lactose, palatinose, raffinose, lactosucrose, glucosylsucrose, galactosyl-sucrose, xylobiose, etc. Preferably, the saccharide moiety is based on a monosaccharide, most preferably glucose;

X represents a linear or branched, saturated or unsaturated, C1 to C40 hydrocarbon-based group, possibly containing in their chain one or more oxygen, sulphur and/or nitrogen atoms. Preferably, X represents a linear, unsubstituted alkyl group containing at least one N atom, most preferably a linear, unsubstituted alkyl group having 1-6 carbon atoms and at least one N atom;

D represents a silicone based group of the formula R2SiO, where R2 represents a linear or branched, saturated or unsaturated, C1 to C10 hydrocarbon-based group. Preferably, R2 is an unsubstituted C1 to C3 alkyl group (methyl, ethyl, propyl), most preferably a methyl group; and n represents a number between 1 and 1000, preferably between 100 and 500, more preferably between 250 and 400, and more preferably between 300 and 350, including all ranges and subranges therebetween.

Preferably, such sugar silicone surfactants are prepared by reacting a lactone form of the saccharide with an amino form of the D group, thereby forming an alkyl group X having an N atom between the saccharide moiety and the silicone moiety.

Particularly preferred sugar silicone surfactants include gluconamidoethylaminopropylsilicone, sold as DC CE 8810, available from DOW CORNING and lactobionolactonesiloxane.

Preferably, the sugar silicone surfactant is employed in an amount ranging from about 0.1 to about 10% of the total weight of the composition, more preferably from about 0.2 to about 8% of the total weight of the composition, and most preferably from about 0.3 to about 5%, including all ranges and subranges therebetween, all weights based on the total weight of the composition.

Oils

The composition of the present invention also contains at least one oil. Any oil can be used in accordance with the present invention. The oil can be volatile or non-volatile, silicone-based and/or hydrocarbon-based, etc. Thus, for example, the oil component may contain, independently or in combination, volatile silicone oils, non-volatile silicone oils, volatile non-silicone oils and non-volatile non-silicone oils.

According to one embodiment, the oil phase may contain one or more volatile silicone oils. Examples of such volatile silicone oils include linear or cyclic silicone oils having a viscosity at room temperature less than or equal to 6 cSt and having from 2 to 7 silicone atoms, these silicones being optionally substituted with alkyl or alkoxy groups of 1 to 10 carbon atoms. Suitable oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3St) from Dow Corning | 102 | 3 |

Further, a volatile linear silicone oil may be employed in the compositions of the present invention. Suitable volatile linear silicone oils include those described in U.S. Pat. No. 6,338,839 and WO03/042221, the contents of which are incorporated herein by reference. The volatility of the solvents/oils can be determined using the evaporation speed as set forth in U.S. Pat. No. 6,338,839, also incorporated herein by reference.

Examples of other silicone oils that may be used in the invention include non-volatile linear polydimethylsiloxanes (PDMSs), that are liquid at room temperature; polydimethylsiloxanes comprising alkyl, alkoxy or phenyl groups, which are pendent and/or at the end of a silicone chain, these groups each containing from 2 to 24 carbon atoms; phenylsilicones, for instance phenyl trimethicones, phenyl dimethicones, phenyl trimethylsiloxydiphenylsiloxanes, diphenyl dimethicones, diphenyl methyldiphenyl trisiloxanes and 2-phenylethyl trimethylsiloxysilicates.

According to other preferred embodiments, the oil phase may contain one or more non-silicone volatile oils and may be selected from volatile hydrocarbon oils, alcohols, volatile esters and volatile ethers. Examples of such volatile non-silicone oils include, but are not limited to, volatile hydrocarbon oils having from 8 to 16 carbon atoms and their mixtures and in particular branched C8 to C16 alkanes such as C8 to C16 isoalkanes (also known as isoparaffins), isododecane, isodecane, isohexadecane, and for example, the oils sold under the trade names of Isopar or Permethyl, the C8 to C16 branched esters such as isohexyl or isodecyl neopentanoate and their mixtures. Preferably, the volatile non-silicone oils have a flash point of at least 40° C.

Non-limiting examples of volatile non-silicone oils are listed in Table 2 below.

TABLE 2

| Compound | Flash Point (° C.) |
|---|---|
| Isododecane | 43 |
| Isohexadecane | 102 |
| Isodecyl Neopentanoate | 118 |
| Propylene glycol n-butyl ether | 60 |

TABLE 2-continued

| Compound | Flash Point (° C.) |
|---|---|
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

Examples of other non-silicone oils which can be used in the compositions of the present invention include polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names MIGLYOL 810, 812 and 818 by the company Dynamit Nobel;

synthetic oils or esters of formula R5COOR6 in which R5 represents a linear or branched higher fatty acid residue containing from 1 to 40 carbon atoms, including and better still from 7 to 19 carbon atoms, and R6 represents a branched hydrocarbon-based chain containing from 1 to 40 carbon atoms, including and better still from 3 to 20 carbon atoms, with R6+R7, such as, for example, Purcellin oil (cetostearyl octanoate), isononyl isononanoate, C12 to C15 alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; C8 to C26 fatty alcohols, for instance oleyl alcohol; and mixtures thereof.

In an embodiment of the present invention, a preferred oil is a non-volatile ester, more preferably, octyl palmitate.

Preferably, the oil is employed in an amount ranging from about 1.0 to about 35% by weight, preferably from about 5 to about 25% by weight, and more preferably from about 10 to about 15% by weight, including all ranges and subranges therebetween, all weights based on the total weight of the composition.

Water

The composition of the present invention also contains water in order to form an emulsion, preferably an oil-in-water emulsion.

Thus, for example, in an oil-in-water emulsion, the water is typically present in an amount of from about 40 to about 80% by weight, preferably from about 45 to about 70% by weight, and more preferably from about 50 to about 60% by weight, including all ranges and subranges therebetween, all weights based on the total weight of the composition.

It should be noted, however, that while the composition of the present invention is preferably in the form of an oil-in-water emulsion, the invention is intended to encompass water-in-oil emulsions, multiple emulsions, nanaoemulsions, etc. as well. Thus, for example, in the case of water-in-oil emulsions, the water is present in an amount of from about 20 to about 50% by weight, preferably from about 22 to about 45% by weight, and more preferably from about 25% to about 40% by weight, including all ranges and subranges therebetween, all weights based on the total weight of the composition.

Emulsifiers

According to preferred embodiments, compositions which employ a polyorganosiloxane-containing polymer and/or a sugar silicone surfactant as the softening agent further comprise an emulsifier. However, in a composition that employs a cationic surfactant, an anionic surfactant, a nonionic esterified sugar surfactant, and mixtures thereof, an emulsifier is optional.

Examples of suitable emulsifiers include: fatty acids, fatty alcohols, polyethoxylated fatty alcohols or polyglycerolated fatty alcohols, such as polyethoxylated stearyl alcohols or cetylstearyl alcohols; C16-C30 fatty acids neutralized by amines, ammonia or the alkali metal salts thereof; quaternary amines, amine oxides and amines, e.g., alkyl amines, alkyl imidazolines, ethoxylated amines, quaternary compounds, and quaternized esters.

Phospholipid emulsifiers can also be used herein. A phospholipid is a compound which on hydrolysis yields phosphoric acid, an alcohol, fatty acid, and a nitrogenous base. They are widely distributed in nature and include such substances as lecithin, cephalin, and sphingomyelin. Further, alkyl modified silicone emulsifiers may also be used. Examples include, but are not limited to, PEG-9 polydimethylsiloxyethyl dimethicone, PEG/PPG-10/3 oleyl ether dimethicone and PEG-9 polydimethylsiloxyethyl dimethicone.

If present, the emulsifier is preferably employed in an amount ranging from about 0.5 to about 5% by weight, preferably from about 1 to about 4% by weight, and more preferably from about 1.5 to about 3% by weight, including all ranges and subranges therebetween, all weights based on the total weight of the composition.

Auxiliaries

Various types of auxiliary ingredients may also be used in the composition of the present invention. Suitable active ingredients include, for example, co-emulsifiers; film-forming polymers; co-solvents; colorants such as pigments, inks and lakes; dermatological ingredients such as sunscreen agents, anti-acne agents, anti-aging compounds; insect repelling agents; transdermal pharmaceutical compounds; deodorant and antiperspirant agents; perfumes; dye compounds; etc. The type and amount of optional ingredient to be employed will depend on the composition's ultimate use, and is to be determined by those of ordinary skill in the art.

Personal care compositions which may be formulated using the composition of the present invention can include, but are not limited to, colored cosmetics such as foundation, eyeshadow, blush; deodorants; antiperspirants; lotions; sunscreens; moisturizers; and the like.

According to preferred embodiments, methods of softening a composition comprising agar which comprise adding at least one of the above identified softening agents are also provided.

According to preferred embodiments, methods of making the invention compositions are also provided. These methods comprise mixing together: (a) at least one thermo-reversible polysaccharide chosen from agar; (b) at least one of the above-identified softening agents; (c) at least one oil; and (d) water. Preferably, the composition is prepared such that it has a soft texture, good pickup and a desirable aesthetic appearance.

The present invention is further described in terms of the following non-limiting example. Unless otherwise indicated, all parts and percentages are on a weight-by-weight percentage basis.

EXAMPLES

Example 1

Composition Containing Cationic Surfactant

| Phase | CTFA Name | % wt/wt |
|---|---|---|
| A | Di Water | 59.11 |
| | Agar | 1 |
| | Disodium EDTA | 0.05 |
| | PEG-7 Glyceryl Cocoate | 1 |
| | UnTreated Pigments | 15 |
| | Mica | 2 |
| | Humectants | 5.57 |
| | Preservatives | 0.77 |
| B | Octyl Palmitate | 13 |
| | Behentrimonium Chloride | 2 |
| C | Silica | 0.5 |
| | TOTAL | 100 |

Example 2

Composition Containing Anionic Surfactant

| Phase | CTFA Name | % wt/wt |
|---|---|---|
| A | Di Water | 59.11 |
| | Sodium Laureth Sulfate | 2 |
| | Agar | 1 |
| | Disodium EDTA | 0.05 |
| | PEG-7 Glyceryl Cocoate | 1 |
| | UnTreated Pigments | 15 |
| | Mica | 2 |
| | Humectants | 5.57 |
| | Preservatives | 0.77 |
| B | Octyl Palmitate | 13 |
| C | Silica | 0.5 |
| | TOTAL | 100 |

Example 3

Composition Containing Mixture of Esterified Sugar Surfactant and Anionic Surfactant

| Phase | CTFA Name | % wt/wt |
|---|---|---|
| A | Di Water | 56.08 |
| | Agar | 1 |
| | Disodium EDTA | 0.05 |
| | PEG-7 Glyceryl Cocoate | 1 |
| | UnTreated Pigments | 15 |
| | Mica | 2 |
| | Glycerin | 5.57 |
| | Phenoxyethanol | 0.8 |
| | Sodium Laureth Sulfate | 0.5 |
| B | Octyl Palmitate | 13 |
| | Cetyl Alcohol | 0.5 |
| | MONTANOV ®: C14-22 ALCOHOLS (and) C12-20 ALKYL GLUCOSIDE | 2 |
| | Dextrin Palmitate | 2 |
| C | Silica | 0.5 |
| | TOTAL | 100 |

Example 4

Composition Containing Esterified Sugar Surfactant

| Phase | CTFA Name | % wt/wt |
|---|---|---|
| A | Di Water | 57.61 |
| | Agar | 1 |
| | Sucrose Stearate | 1 |
| | Disodium EDTA | 0.05 |
| | PEG-7 Glyceryl Cocoate | 1 |
| | UnTreated Pigments | 15 |
| | Mica | 2 |
| | Humectants | 5.57 |
| | Preservatives | 0.77 |
| B | Octyl Palmitate | 13 |
| | Cetyl Alcohol | 0.5 |
| | MONTANOV ®: C14-22 Alcohol and C12-20 Alkylglucoside | 2 |
| C | Silica | 0.5 |
| | TOTAL | 100 |

Example 5

Composition Containing Polyorganosiloxane-Containing Polymer

| Phase | CTFA Name | % wt/wt |
|---|---|---|
| A | Di Water | 57.61 |
| | Agar | 1 |
| | Disodium EDTA | 0.05 |
| | PEG-7 Glyceryl Cocoate | 1 |
| | UnTreated Pigments | 15 |
| | Mica | 2 |
| | Humectants | 5.57 |
| | Preservatives | 0.77 |
| B | Octyl Palmitate | 13 |
| | NYLON-611/DIMETHICONE COPOLYMER | 1 |
| | Cetyl Alcohol | 0.5 |
| | MONTANOV ®: C14-22 Alcohol and C12-20 Alkylglucoside | 2 |
| C | Silica | 0.5 |
| | TOTAL | 100 |

Example 6

Composition containing Sugar Silicone Surfactant

| Phase | CTFA Name | % wt/wt |
| --- | --- | --- |
| A | Di Water | 56.61 |
|   | Agar | 1 |
|   | GLUCONAMIDOETHYLAMINOPROPYLSILICONE (and) ALCOHOL | 2 |
|   | Disodium EDTA | 0.05 |
|   | PEG-7 Glyceryl Cocoate | 1 |
|   | UnTreated Pigments | 15 |
|   | Mica | 2 |
|   | Humectants | 5.57 |
|   | Preservatives | 0.77 |
| B | Octyl Palmitate | 13 |
|   | Cetyl Alcohol | 0.5 |
|   | MONTANOV ®: C14-22 Alcohol and C12-20 Alkylglucoside | 2 |
| C | Silica | 0.5 |
|   | TOTAL | 100 |

Procedure
1. Added phase A to the main kettle and heated to 90° C. while grinding.
2. In a separate beaker, heated phase B to 75-80° C. and mixed until uniform.
3. Combined phase A and phase B while homogenizing at 75-80° C.
4. Added phase C to main kettle and mixed.
5. Cooled to 40° C.

The same procedure was used for all examples.
The above-identified compositions all had a rich, creamy texture/light feel, good pickup and desirable aesthetic properties. In addition, the compositions' reduced rigidity allowed the cited optional ingredients to be easily blended therewith.

The invention claimed is:

1. An oil-in-water composition, comprising:
 a) an aqueous phase comprising water and at least one thermo-reversible polysaccharide chosen from agar; and
 b) an oil phase consisting of octyl palmitate; a softening agent selected—from the group consisting of a cationic surfactant, an anionic surfactant, a nonionic esterified sugar surfactant, a polyorganosiloxane-containing polymer, a sugar silicone surfactant, and a mixture thereof: and optionally a fatty alcohol emulsifier;
 wherein the oil-in-water composition is made by mixing the water and the thermoreversible polysaccharide to yield an aqueous phase, separately mixing only the octyl palmitate, the softening agent, and the optional fatty alcohol emulsifier wherein the fatty alcohol emulsifer is cetyl alcohol to yield an oil phase, and mixing the aqueous phase and the oil phase to yield an oil-in-water emulsion.

2. The oil-in-water composition of claim 1, wherein the thermo-reversible polymer is present in an amount of from 0.1 to 3% by weight, based on the weight of the oil-in-water composition.

3. The oil-in-water composition of claim 1, wherein the softening agent is selected from the group consisting of a cationic surfactant, an anionic surfactant, a nonionic esterified sugar surfactant, and mixtures thereof.

4. The oil-in-water composition of claim 1, wherein the softening agent is a polyorganosiloxane-containing polymer.

5. The oil-in-water composition of claim 1, wherein the softening agent is a sugar silicone surfactant.

6. The oil-in-water composition of claim 3, wherein the softening agent is present in an amount of from 0.1 to 6% by weight, based on the weight of the oil-in-water composition.

7. The oil-in-water composition of claim 4, wherein the softening agent is present in an amount of from 0.2 to 10% by weight, based on the weight of the oil-in-water composition.

8. The oil-in-water composition of claim 5, wherein the softening is present in an amount of from 0.1 to 10% by weight, based on the weight of the oil-in-water composition.

9. The oil-in-water composition of claim 3, wherein the softening agent is selected from the group consisting of behentrimonium chloride, sodium laureth sulfate, sucrose stearate, dextrin palmitate, and a mixture thereof.

10. The oil-in-water composition of claim 3, wherein the softening agent is a mixture of an anionic surfactant and an nonionic esterified sugar surfactant.

11. The oil-in-water composition of claim 3, wherein the softening agent is behentrimonium chloride and/or sodium laureth sulfate.

12. The oil-in-water composition of claim 4, wherein the polyorganosiloxane-containing polymer is a nylon 611/dimethicone copolymer.

13. The oil-in-water composition of claim 5, wherein the softening agent is gluconamidoethylaminopropylsilicone and/or lactobionolactonesiloxane.

14. The oil-in-water composition of claim 1, wherein the octyl palmitate is present in an amount of from 1 to 35% by weight, based on the weight of the oil-in-water composition.

15. A process for softening an oil-in-water emulsion containing agar, the method comprising:
 mixing water and a thermo-reversible polysaccharide chosen from agar to yield an aqueous phase, separately mixing only octyl palmitate, a softening agent, and optionally a fatty alcohol emulsifier to yield an oil phase, and mixing the aqueous phase and the oil phase to yield an oil-in-water emulsion, wherein the softening agent is selected from the group consisting of a cationic surfactant, an anionic surfactant, a nonionic esterified sugar surfactant, a polyorganosiloxane-containing polymer, a sugar silicone surfactant, and a mixture thereof.

* * * * *